(12) United States Patent
Matsumoto et al.

(10) Patent No.: US 8,247,117 B2
(45) Date of Patent: Aug. 21, 2012

(54) IONIC LIQUID

(75) Inventors: Hajime Matsumoto, Ikeda (JP);
Zhi-Bin Zhou, Ikeda (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 1188 days.

(21) Appl. No.: 11/794,179

(22) PCT Filed: Nov. 22, 2005

(86) PCT No.: PCT/JP2005/021473
§ 371 (c)(1),
(2), (4) Date: Jun. 26, 2007

(87) PCT Pub. No.: WO2006/070545
PCT Pub. Date: Jul. 6, 2006

(65) Prior Publication Data
US 2008/0008930 A1 Jan. 10, 2008

(30) Foreign Application Priority Data

Dec. 27, 2004 (JP) ................................ 2004-375173

(51) Int. Cl.
*H01M 6/18* (2006.01)
(52) U.S. Cl. ........ 429/307; 429/122; 429/336; 429/326; 429/330; 429/328
(58) Field of Classification Search .................. 429/122, 429/336, 326, 330, 328
See application file for complete search history.

(56) References Cited

U.S. PATENT DOCUMENTS

| | | | |
|---|---|---|---|
| 7,709,656 B2 | 5/2010 | Welz-Biermann et al. | |
| 2002/0160261 A1 | 10/2002 | Schmidt et al. | |
| 2002/0172865 A1 | 11/2002 | Che et al. | |
| 2003/0013021 A1* | 1/2003 | Wariishi ........................ | 429/307 |
| 2003/0080312 A1* | 5/2003 | Seddon et al. .................... | 252/1 |
| 2007/0265453 A1* | 11/2007 | Welz-Biermann et al. ......................... | 548/331.5 |

FOREIGN PATENT DOCUMENTS

| | | |
|---|---|---|
| DE | 10325051 A1 | 12/2004 |
| JP | 2002-063934 A | 2/2002 |
| JP | 2002-099001 A | 4/2002 |
| JP | 2002-305024 A | 10/2002 |
| JP | 2003-132945 A | 5/2003 |
| JP | 2003-331918 A | 11/2003 |
| JP | 2004-123631 A | 4/2004 |
| WO | WO 01/15175 A2 * | 3/2001 |
| WO | WO 2005/063773 A1 | 7/2005 |

OTHER PUBLICATIONS

Frohn, H-J, et al. "(Fluororgano)fluoroboranes and -fluoroborates. 2 [1]. Synthesis and Spectroscopic characterization of Potassium Polyfluoroalken-l-yltrifluoroborates." Z. Anorg Allg. Chem., 2001, 627, 2499-2405.*
Frohn, H-J, et al "A Preparative Method for Perfluoroalkyltrifluoroborates and Perfluoroalkyldifluoroboranes" Z. Anorg Allg. Chem., 2001, 627, 15-16.*
Frohn, H-J, et al. "(Fluororgano)fluoroboranes and -fluoroborates. 6 [1]."The Reactivity of Potassium perfluoroalkyltrifluoroborates and Their Hydrocarbon Analogues towards Acids of Different Strength: a Systematic Study of the Hydrodeboration. Z. Anorg Allg. Chem., 2002, 628, 883-890.*
Zhi-Bin Zhou et al. "Novel electrolyte salts based on perfluoroalkyltrifloroborate anions. 1. Synthesis and characterization.". J. Fluorine Chem., 2003, 123, 127-131.*
Germany Office Action dated Jun. 11, 2010, issued in corresponding Germany Patent Application No. 11-2005-003-198.
Batey, Robert A. et al.; "Synthesis and cross-coupling reactions of tetraalkylammonium organotrifluoroborate salts"; Tetrahedron Letters, vol. 42, accepted Oct. 22, 2001 pp. 9099-9103.
International Search Report of PCT/JP2005/021473, date of mailing Feb. 28, 2006.
Japanese Office Action dated Dec. 7, 2010, issued in corresponding Japanese Patent Application No. 2006-550625.
Thadani, Avinash N. et al.; "A Mild Protocol for Allylation and Highly Diastereoselective Syn or Anti Crotylation of Aldehydes in Biphasic and Aqueous Media Utilizing Potassium Allyl- and Crotyltrifluoroborates"; Organic Letters, Sep. 19, 2002, vol. 4, No. 22, pp. 3827-3830.
Z. Zhou et al., "Structure and Properties of New Ionic Liquids Based on Alkyl- and Alkenyltrifluoroborates", ChemPhysChem, Jun. 2005, pp. 1324-1332.
Z. Zhou et al., "Novel Ionic Liquids Based on Organotrifluroborates with Various Cations", 72th Convention of the Electrochemical Society of Japan, Apr. 1, 2005, p. 139.

* cited by examiner

*Primary Examiner* — Patrick Ryan
*Assistant Examiner* — Alex Usyatinsky
(74) *Attorney, Agent, or Firm* — Westerman, Hattori, Daniels & Adrian, LLP

(57) ABSTRACT

The present invention relates to ionic liquids having low melting points, low viscosities and high electrical conductivities; and more specifically, to ionic liquids including at least one organic onium ion and at least one anion represented by the formula: $[Z-BF_3]^-$, wherein Z is an alkyl group, an alkenyl group, or a fluoroalkenyl group. The ionic liquids according to the invention are capable of easily dissolving electrolytes such as lithium salts, and are also nonflammable and have low viscosities; therefore, the ionic liquids are suitable for use as electrolyte solvents for lithium batteries such as lithium secondary batteries, electric double-layer capacitors, and the like. The ionic liquids according to the invention are suitable for use in electrochemical devices such as lithium secondary batteries, fuel cells, solar batteries, electrical double-layer capacitors and the like; as solvents for chemical reactions; and as lubricants.

5 Claims, No Drawings

IONIC LIQUID

TECHNICAL FIELD

The present invention relates to ionic liquids, and more particularly to ionic liquids with low viscosities and high electrical conductivities. The present invention also relates to lithium batteries (lithium secondary batteries, in particular) and electric double-layer capacitors which comprise the ionic liquids.

BACKGROUND ART

Ionic liquids, also referred to as room-temperature-molten salts, have attracted special attention for the past several years, owing to their potential uses as electrolytes for a variety of electrochemical devices such as lithium secondary batteries, solar cells, actuators, electric double-layer capacitors and the like, reaction media, and catalysts for organic syntheses. Compared with conventional organic liquid electrolytes, ionic liquids as electrolytes have the main advantages of flame retardance, non-volatility and high thermal stability. Bistrifluoromethylsulfonylimide ($[(CF_3SO_2)_2N]^-$) and tetrafluoroborate ($BF_4^-$) have attracted attention as anions for most of the ionic liquids so far reported, because of their high electrochemical stabilities and thermal stabilities (Patent Documents 1 and 2). However, ionic liquids containing these anions have suffered from problems such as, in particular, low conductivities at low temperatures.

Patent Document 3 discloses boron compounds; however, for example, triethylmethylammonium $CF_3BF_3$ manufactured in the Examples has a melting point as high as 181° C., and therefore is not an ionic liquid. Moreover, Patent Publication 4 discloses the $BF_3CF_3$ salt of 1-ethyl-3-methylimidazolium in Example 1.

Patent Document 1: Japanese Unexamined Patent Application Publication No. 2002-099001
Patent Document 2: Japanese Unexamined Patent Application Publication No. 2003-331918
Patent Document 3: Japanese Unexamined Patent Application Publication No. 2002-63934
Patent Document 4: Japanese Unexamined Patent Application Publication No. 2004-123631

DISCLOSURE OF THE INVENTION

Problem to be Solved by the Invention

An object of the present invention is to provide ionic liquids with low viscosities, low melting points and high electrical conductivities by improving the anionic components.

Means for Solving the Problem

In view of the aforementioned problems, the present inventors conducted extensive research, and found that an ionic liquid with a low viscosity, a low melting point, and a high electrical conductivity at low temperatures can be attained using at least one anion represented by $[Z-BF_3]^-$, wherein Z is an alkyl group, an alkenyl group, or a fluoroalkenyl group, or a solid salt containing such an anion.

The present invention provides ionic liquids and anions therefor, a process for preparing the ionic liquids, and lithium batteries and capacitors using the ionic liquids, as set forth in the following Items:

1. An ionic liquid comprising at least one organic onium ion; and at least one anion represented by $[Z-BF_3]^-$, wherein Z is an alkyl group, an alkenyl group, or a fluoroalkenyl group.
2. An ionic liquid according to Item 1, wherein Z is a $C_{1-5}$ alkyl, vinyl, or perfluorovinyl group.
3. An ionic liquid according to Item 1 or 2, wherein the cation is a 1-methyl-3-ethylimidazolium cation.
4. An electrical double-layer capacitor, comprising an ionic liquid according to any of Items 1 to 3.
5. A lithium battery comprising an ionic liquid according to any one of Items 1 to 3.
6. A process for preparing an ionic liquid, comprising mixing a compound including at least one organic onium compound with a compound including, as an anionic component, at least one anion represented by $[Z-BF_3]^-$, wherein Z is an alkyl group, a vinyl group ($CH_2=CH$), or a perfluorovinyl group ($CF_2=CF$).

Effects of the Invention

The ionic liquids according to the invention have properties such as low viscosities and high electrical conductivities, and are suitable for use in electrochemical devices such as lithium secondary batteries, fuel cells, solar batteries, electrical double-layer capacitors and the like; as solvents for chemical reactions; and as lubricants.

BEST MODE FOR CARRYING OUT THE INVENTION

The ionic liquids for use in the invention typically have melting points of 150° C. or less, preferably 80° C. or less, more preferably 60° C. or less, still more preferably 40° C. or less, and even more preferably 25° C. or less. For example, ionic liquids with melting points of 150° C. or less can find a wide range of uses in fuel cells. On the other hand, ionic liquids for use in energy devices such as solar cells, lithium batteries, capacitors, etc., electrochromic devices, and electrochemical devices such as electrochemical sensors, etc., preferably have melting points of room temperature (25° C.) or less, and more preferably 0° C. or less.

In the invention, at least one anion represented by $[Z-BF_3]^-$, wherein Z is an alkyl group, an alkenyl group, or a fluoroalkenyl group, is used as an anion component of an ionic liquid.

Examples of alkyl groups include $C_{1-6}$, and preferably $C_{1-4}$, straight or branched alkyl groups, such as methyl, ethyl, n-propyl, isopropyl, n-butyl, isobutyl, sec-butyl, tert-butyl, pentyl, hexyl and the like.

Examples of alkenyl groups include $C_{1-6}$ alkenyl groups such as vinyl ($CH_2=CH$), allyl ($CH_3CH_2=CH$), 1-butenyl, 2-butenyl, 1,1-dimethylvinyl (($CH_3)_2C=CH_2$) and the like; preferable examples being $C_{1-4}$ alkenyl groups.

Examples of fluoroalkenyl groups include $C_{1-6}$ fluoroalkenyl groups such as perfluorovinyl ($CF_2=CF$), monofluorovinyl groups, 2,2-difluorovinyl ($CF_2=CH$), perfluoroallyl ($CF_3CF_2=CF$), perfluoro-1-butenyl, perfluoro-2-butenyl, 1,1-ditrifluoromethyl-2-fluorovinyl (($CF_3)_2C=CF_2$), perfluoropentenyl, perfluorohexenyl and the like; preferable examples being $C_{1-4}$ fluoroalkenyl groups. The anion can be prepared according to processes disclosed in the known literature: S. Darses, G. Michaud and J. P. Genet, *Tetrahedron Lett.*, 1998, 39, 5045; G. A. Molander and M. R. Rivero, *Org. Lett.*, 2002, 4, 107; G. A. Molander and M. R. Rivero, *J. Org. Chem.*, 2002, 67, 8424; G. A. Molander and T. Ito, *Org. Lett.*, 2001, 3, 393; G. A. Molander, C. S. Yun, M. Ribagorda and B.

Biolatto, *J. Org. Chem.*, 2003, 68, 5534; H. J. Frohn and V. V. Bardin, *Z. Anorg. Allg. Chem.*, 2001, 627, 2499; S. Darses and J. P. Genet, *Eur. J. Org. Chem.*, 2003, 35, 4313.

The ionic liquid according to the invention may comprise a single anionic component, or may comprise two or more anionic components to further decrease the melting point.

The ionic liquid can be produced by mixing an organic onium compound with a salt of at least one anion represented by $[Z-BF_3]^-$, wherein Z is an alkyl group, an alkenyl group, or a fluoroalkenyl group, and a cationic component, such as an alkaline-metal ion ($Na^+$, $K^+$, $Li^+$, $Cs^+$, etc.), an alkaline-earth metal ion ($Ca^{2+}$, $Mg^{2+}$, $Ba^{2+}$, etc.), $H^+$, $Bu_3Sn^+$ or the like; and separating the resulting ionic liquid containing the organic onium ion and $[Z-BF_3]^-$, wherein Z is an alkyl group, an alkenyl group, or a fluoroalkenyl group, which is formed via an ion-exchange reaction. For example, such an ionic liquid containing an organic onium ion and $[Z-BF_3]^-$, wherein Z is an alkyl group, an alkenyl group, or a fluoroalkenyl group, can be preferably prepared by mixing [organic onium]$^+$[OH]$^-$ with $[Z-BF_3]^-H^+$, wherein Z is an alkyl group, an alkenyl group, or a fluoroalkenyl group, which are obtained by passing them through an ion-exchange resin; and removing the water. When it is possible to extract the desired molten salt, the salt-exchange reaction for obtaining the ionic liquid can be carried out by solvent extraction.

Examples of organic onium ions include ammonium, guanidinium, phosphonium, oxonium and sulfonium. Among these examples, ammonium, guanidinium, phosphonium and sulfonium are preferable; ammonium, guanidinium and phosphonium are more preferable; and ammonium is still more preferable.

Although an organic onium ion may be used singly, a combination of two or more organic onium ions further reduces the melting point and the viscosity of the resulting ionic solution.

Moreover, the anion of the ionic liquid may be used together with other anion(s), as long as $[Z-BF_3]^-$, wherein Z is an alkyl group, an alkenyl group, or a fluoroalkenyl group, is a principal component. The condition that $[Z-BF_3]^-$ is a principal component means that the content of $[Z-BF_3]^-$ in the ionic liquid is highest of all the anionic components. The proportion of $[Z-BF_3]^-$ to all the anionic components is preferably 34 wt % or more, more preferably 50 wt % or more, and still more preferably 60 wt % or more.

Examples of other anions include $BF_4$, $PF_6$, TFSI (($CF_3SO_2)_2N^-$), $CF_3SO_3^-$, $CF_3COO^-$, $CH_3SO_3^-$, $N(CN)_2^-$ and the like.

Various examples of organic onium compounds are described below:

(1) Ammonium represented by general formula (Ia):

$$[R^4-NR^1R^2R^3]^+ \quad (Ia)$$

wherein each of $R^1$, $R^2$ and $R^3$, which may be the same or different, is a hydrogen atom, an alkyl group, a haloalkyl group, an alkoxy group, an alkylthio group, a polyether group, an optionally substituted aryl group, an optionally substituted aralkyl group, an alkoxyalkyl group, or a heterocyclic group; $R^1$ and $R^2$, taken together with the nitrogen atom, may form an optionally substituted 5- to 8-membered nitrogen-containing heterocyclic group; $R^4$ is an alkyl group, a haloalkyl group, an alkoxy group, a polyether group, an optionally substituted aryl group, an optionally substituted aralkyl group, or an alkoxyalkyl group; a organic functional group having redox properties; or a group derived from a volatile organic solvent.

(2) Guanidinium represented by general formula (Ib):

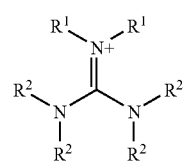

(Ib)

wherein $R^1$ and $R^2$ are the same as defined in formula (Ia).

(3) Phosphonium represented by general formula (Ic):

$$[R^4-PR^1R^2R^3]^+ \quad (Ic)$$

wherein $R^1$, $R^2$, $R^3$ and $R^4$ are the same as defined in formula (Ia); provided that $R^1$ and $R^2$, taken together with the phosphorus atom, may form an optionally substituted 5- to 8-membered phosphorus-containing heterocyclic group.

(4) Oxonium represented by general formula (Id):

$$[R^4-OR^1R^2]^+ \quad (Id)$$

wherein $R^1$, $R^2$ and $R^4$ are the same as defined in formula (Ia); provided that $R^1$ and $R^2$, taken together with the oxygen atom, may form an optionally substituted 5- to 8-membered oxygen-containing heterocyclic group.

(5) Sulfonium represented by general formula (Ie):

$$[R^4-SR^1R^2]^+ \quad (Ie)$$

wherein $R^1$, $R^2$ and $R^4$ are the same as defined in formula (Ia); provided that $R^1$ and $R^2$, taken together with the sulfur atom, may form an optionally substituted 5- to 8-membered sulfur-containing heterocyclic group.

Examples of organic onium compounds include salts of organic onium cations with the halogen ion, nitrate ion, sulfate ion, phosphate ion, perchloride ion, methanesulfonate ion, toluenesulfonate ion and like ions.

Alternatively, the ionic liquid may be produced using an organic onium ion (in the form of, for example, a halide salt or a sulfate salt) and at least one anion (in the form of, for example, a silver salt, a calcium salt or a barium salt) represented by $[Z-BF_3]^-$, wherein Z is an alkyl group, an alkenyl group, or a fluoroalkenyl group, to form a sparingly soluble salt, such as a silver halide, barium sulfate or calcium sulfate resulting from the aforementioned counterions, and removing the formed salt.

Examples of alkyl groups in organic onium salts include $C_{1-20}$, preferably $C_{1-10}$, more preferably $C_{1-6}$, and still more preferably $C_{1-3}$, straight or branched alkyl groups, such as methyl, ethyl, n-propyl, isopropyl, n-butyl, sec-butyl, isobutyl, tert-butyl, pentyl, hexyl, heptyl, octyl, nonyl, decyl, undecyl, dodecyl, tridecyl, tetradecyl, hexadecyl, octadecyl, eicosyl, and the like.

Examples of haloalkyl groups include $C_{1-20}$, preferably $C_{1-10}$, more preferably $C_{1-6}$, and still more preferably $C_{1-3}$, haloalkyl groups resulting from the substitution of at least one hydrogen atom of any of the aforementioned alkyl groups with a halogen atom (chlorine, bromine, fluorine or iodine), and preferably with a fluorine atom.

Examples of alkoxy groups include $C_{1-20}$, preferably $C_{1-10}$, more preferably $C_{1-6}$, and still more preferably $C_{1-3}$, straight or branched alkoxy groups with the structure [O-an alkyl mentioned above].

Examples of alkylthio groups include $C_{1-20}$, preferably $C_{1-10}$, more preferably $C_{1-6}$, and still more preferably $C_{1-3}$, straight or branched alkoxy groups with the structure [S-an alkyl mentioned above].

Examples of aryl groups include $C_{6-14}$, and preferably $C_{6-10}$, aryl groups such as phenyl, toluyl, xylyl, ethylphenyl, 1,3,5-trimethyl phenyl, naphthyl, anthranil, phenanthryl, and like groups.

Examples of aralkyl groups include $C_{7-15}$ aralkyl groups such as benzyl, phenethyl, and naphthylmethyl groups.

The alkoxy and alkyl groups of alkoxyalkyl groups are the same as mentioned above. Examples of alkoxyalkyl groups include $C_{1-20}$, preferably $C_{1-10}$, more preferably $C_{1-6}$, and still more preferably $C_{1-3}$, straight or branched alkyl groups substituted with $C_{1-20}$, preferably $C_{1-10}$, more preferably $C_{1-6}$, and still more preferably $C_{1-3}$, straight or branched alkoxy groups. Preferable examples among them are methoxymethyl ($CH_2OCH_3$), methoxyethyl ($CH_2CH_2OCH_3$), ethoxymethyl ($CH_2OCH_2CH_3$), and ethoxyethyl ($CH_2CH_2OCH_2CH_3$) groups.

Examples of polyether groups include polyether groups represented by —$(CH_2)_{n1}$—O—$(CH_2CH_2O)_{n2}$—($C_{1-4}$ alkyl) or —$(CH_2)_{n1}$—O—$(CH_2CH(CH_3)O)_{n2}$—($C_{1-4}$ alkyl), wherein n1 is an integer from 1 to 4; n2 is an integer from 1 to 4; and the $C_{1-4}$ alkyl is, for example, methyl, ethyl, n-propyl, isopropyl, n-butyl, isobutyl, sec-butyl, or tert-butyl.

Moreover, $R^1$ and $R^2$, taken together with the nitrogen atom linked to them, may form a 5- to 8-membered, and preferably a 5- or 6-membered, nitrogen-containing heterocyclic group (pyrrolidinium, piperidinium, pyrrolinium, pyridinium, imidazolium or the like).

Examples of substituents for aryl and aralkyl groups include halogen atoms (F, Cl, Br and I), hydroxy groups, methoxy groups, nitro groups, acetyl groups, acetylamino groups and the like.

The aforementioned alkyl groups or alkenyl groups may have one or more of —O—, —COO— and —CO— interposed between C—C single bonds at any positions to form ether, ester, or ketone structures.

Specific examples of ionic liquids prepared using the organic onium compounds according to formula (Ia), wherein $R^4$ is a organic functional group having redox properties, are compounds according to the following formulae (II) to (VIII):

formulae (II) and (III)

(II)

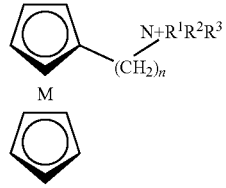

(III)

wherein n is 0 or 1; M is a transition metal; each of $R^1$, $R^2$ and $R^3$, which may be the same or different, is an alkyl group, a haloalkyl group, an alkoxy group, an optionally substituted aryl group, an optionally substituted aralkyl group or an alkoxyalkyl group; and $R^1$ and $R^2$, taken together with the nitrogen atom, may form a 5- to 8-membered nitrogen-containing cyclic group.

formulae (IV) to (VIII)

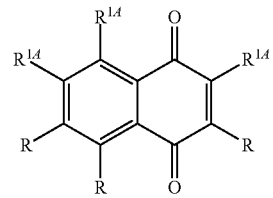

(IV)

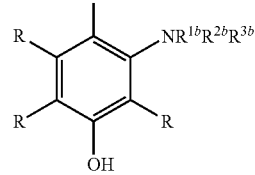

(V)

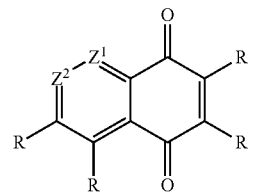

(VI)

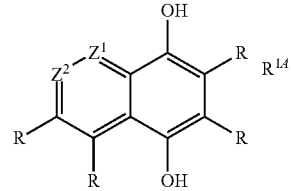

(VIa)

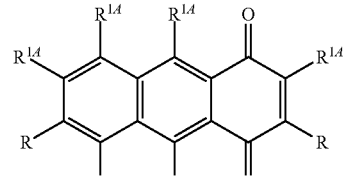

(VII)

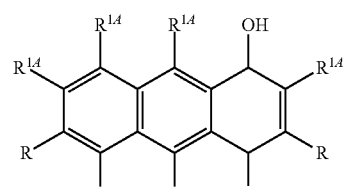

(VIIa)

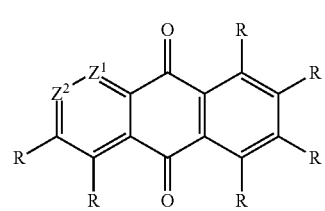

(VIII)

wherein each of the Rs, which may be the same or different, is a halogen atom, an alkyl group, an alkoxy group, an alkanoyl group, a hydroxy group, a carboxyl (COOH) group, an alkoxycarbonyl group, a nitro group, a cyano (CN) group, an acetylamino group, a phenyl group, a benzyl group or a perfluoroalkyl group; alternatively, two adjacent Rs, taken together with the carbon atoms linked to them, may form a benzene ring;

one of the plurality of $R^{1a}$s is $NR^{1b}R^{2b}R^{3b}$, and each of the other $R^{1a}$s, which may be the same or different, is an R; each of $R^{1b}$, $R^{2b}$ and $R^{3b}$, which may be the same or different, is an alkyl group, a haloalkyl group, an alkoxy group, an optionally substituted aryl group, an optionally substituted aralkyl group or an alkoxyalkyl group; provided that $R^{1b}$ and $R^{2b}$, taken together with the nitrogen atom linked to them, may form a 5- to 8-membered nitrogen-containing cyclic group; and one of $Z^1$ and $Z^2$ is CH, and the other is $N^+$—$R^3$, wherein $R^3$ is as defined above.

M represents a transition metal atom, examples of which include Fe, Co, Ni, Zn, Cu, Cr, V, Cd, As, Mn, Ti, Zr, Sn, Ag, In, Hg, W, Pt, Au, Ga, Ge and Ru; a preferable example being Fe.

Examples of halogen atoms include chlorine, fluorine, bromine and iodine atoms.

Examples of alkanoyl groups include $C_{2-21}$ straight or branched alkanoyl groups represented by the formula —CO-(alkyl), wherein the alkyl is as defined above, such as acetyl, propionyl, butyryl and the like.

Examples of alkoxycarbonyl groups include $C_{2-21}$ straight or branched alkoxycarbonyl groups represented by the formula —CO—O(alkyl), wherein the alkyl is as defined above, such as methoxycarbonyl, ethoxycarbonyl, butoxycarbonyl and the like.

Examples of perfluoroalkyl groups include groups in which all of the hydrogen atoms of any of the aforementioned alkyl group are substituted with fluorine atoms, such as, for example, groups represented by $C_nF_{2n+1}$, wherein n is an integer from 1 to 20.

A cationic group in which $R^4$ is a group derived from a volatile organic solvent is introduced into an organic solvent via an alkylene group, as necessary. Examples of organic solvents include compounds that are solid or liquid at room temperature, with boiling points of −100 to 300° C., and preferably 30 to 300° C., at atmospheric pressure. Specific examples of such compounds are as follows:

Ethers: diethyl ether, tetrahydrofuran, tetrahydropyrane, diisopropyl ether, diphenyl ether, anisole, phenetole, guaiacol, etc.

Alkylene glycols: ethylene glycol, propylene glycol, butylene glycol, diethylene glycol, triethylene glycol, etc.

Alkylene glycol monoalkyl ethers: ethylene glycol monomethyl ether, ethylene glycol monoethyl ether, propylene glycol monomethyl ether, propylene glycol monoethyl ether, butylene glycol monomethyl ether, butylene glycol monoethyl ether, diethylene glycol monomethyl ether, diethylene glycol monoethyl ether, etc.

Alkylene glycol dialkyl ethers: ethylene glycol dimethyl ether (DME), ethylene glycol diethyl ether, propylene glycol dimethyl ether, propylene glycol diethyl ether, butylene glycol dimethyl ether, butylene glycol diethyl ether, diethylene glycol dimethyl ether, diethylene glycol diethyl ether, etc.

Esters: methyl acetate, ethyl acetate, propyl acetate, butyl acetate, methyl propionate, ethyl propionate, propyl propionate, butyl propionate, methyl formate, ethyl formate, propyl formate, butyl formate, methyl benzoate, ethyl benzoate, propyl benzoate, butyl benzoate, etc.

Lactones: γ butyrolactone (GBL), etc.

Ketones: acetone (ATN), acetylacetone, methyl ethyl ketone, cyclohexanone, cyclopentanone, etc.

Heteroaromatic hydrocarbons: pyridine, etc.

Alicyclic hydrocarbons: cyclopentane, cyclohexane, methylcyclohexane, etc.

Heteroalicyclic compounds: dioxane, morpholine, pyrrolidine, etc.

Sulfides: dimethyl sulfide, diethyl sulfide, di-n-propylsulfide, diisopropylsulfide, etc.

Carbonates: ethylene carbonate (EC), propylene carbonate (PC), butylene carbonate, diethyl carbonate (DEC), dimethyl carbonate, etc.

Alcohols: ethanol, n-propanol, isopropanol, n-butanol, isobutanol, sec-butanol, tert-butanol, etc.

The above-described cationic group may be introduced into any of these organic solvents by, for example, the processes illustrated below:

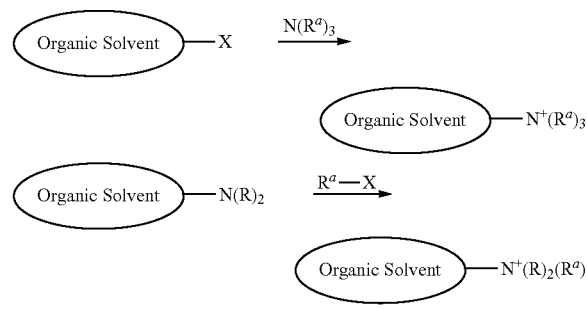

wherein the Organic Solvent is any of the aforementioned organic solvents; each of the $R^a$s, which may be the same or different, is an alkyl group, a haloalkyl group, an alkoxy group, an alkylthio group, a polyether group, an optionally substituted aryl group, an optionally substituted aralkyl group, an alkoxyalkyl group or a heterocyclic group; two of the three $R^a$s, taken together with the nitrogen atom, may form a 5- to 8-membered nitrogen-containing heterocyclic group; R is a hydrogen atom or an optionally substituted alkyl group; and X is a leaving group.

Examples of an optionally substituted alkyl group represented by R include $C_{1-3}$ alkyl groups such as methyl, ethyl, n-propyl, and isopropyl groups; and such an alkyl group may be substituted with a fluorine atom, a methoxy group, a cyano group or a similar group.

X represents a leaving group, and specific examples thereof include a chlorine atom, bromine atom, iodine atom, methane sulfonyl group and p-toluene sulfonyl group.

In one preferred embodiment of the invention, a quaternary ammonium group is introduced into a highly volatile solvent with a low boiling point, so as to form an ionic liquid. In order to produce a quaternary ammonium compound, a leaving group and a tertiary amine may be reacted as explained above, or the amino group of a solvent containing an amino group may be quaternized.

The cationic components mentioned above may be used singly or in combination. When used in combination, the proportion of such cationic components may be set as desired.

Examples of organic ammonium ions suitable for use in the invention are as follows:

Symmetric ammonium cations: tetramethylammonium, tetraethylammonium, tetrapropylammonium cations, etc.

Ammonium cations in which the shortest substituent has carbon atoms of at least 50% and less than 100% of those of the longest substituent (hereinafter also referred to as "pseudo-symmetric"): ethyl trimethylammonium, vinyl trimethylammonium, triethyl methylammonium, triethyl propyl ammonium, diethyldimethylammonium, tributylethylammonium, triethyl isopropyl ammonium, N,N-dimethylpyrrolidinium, N-methyl-N-ethylpyrrolidinium, N-methyl-N-propylpyrrolidinium, N-methyl-N-butylpyrrolidinium, N-methyl-N-ethylpiperidinium, N-methyl-N-propylpiperidinium, N-methyl-N-butylpiperidinium, triethylmethoxymethyl ammonium, dimethylethylmethoxyethyl ammonium, dimethylethylmethoxymethyl ammonium, diethylmethoxyethyl ammonium, diethylmethylmethoxymethyl ammonium cations, etc.

Asymmetric ammonium cations: trimethylpropyl ammonium, trimethylisopropyl ammonium, butyltrimethylammonium, allyltrimethylammonium, hexyltrimethylammonium, octyltrimethylammonium, dodecyltrimethylammonium, triethylmethoxyethoxymethyl ammonium, dimethyldipropyl ammonium cations, etc.

Divalent ammonium cations: hexamethonium cations, etc.

In one preferred embodiment of the invention, the cation of an ionic liquid is as shown below:

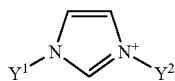

wherein each of $Y^1$ and $Y^2$, which may be the same or different, is methyl, ethyl, n-propyl, isopropyl, n-butyl, isobutyl, sec-butyl, tert-butyl, or benzyl.

Compounds of the formula shown above, in which $Y^1$ is methyl and $Y^2$ is ethyl, are preferred.

The ionic liquids according to the invention are capable of easily dissolving electrolytes such as lithium salts, and are also nonflammable and have low viscosities; therefore, the ionic liquids are suitable for use as electrolyte solvents for lithium batteries such as lithium secondary batteries, electric double-layer capacitors, and the like.

The ionic liquids according to the invention are suitable for use in electrochemical devices such as lithium secondary batteries, fuel cells, solar batteries, electrical double-layer capacitors and the like; as solvents for chemical reactions; and as lubricants.

EXAMPLES

The present invention will be described below in greater detail by way of Examples.

Example 1

(1) Synthesis of Anions

Seven types of anionic potassium salts represented by [Z—$BF_3$]$^-K^+$, wherein Z was $CH_3$, $C_2H_5$, n-$C_3H_7$, n-$C_4H_9$, n-$C_5H_{11}$, $CH_2=CH$, or $CF_2=CF$, respectively, were synthesized according to the processes described in the literature: S. Darses, G. Michaud and J. P. Genet, *Tetrahedron Lett.*, 1998, 39, 5045; G. A. Molander and M. R. Rivero, *Org. Lett.*, 2002, 4, 107; G. A. Molander and M. R. Rivero, *J. Org. Chem.*, 2002, 67, 8424; G. A. Molander and T. Ito, *Org. Lett.*, 2001, 3, 393; G. A. Molander, C. S. Yun, M. Ribagorda and B. Biolatto, *J. Org. Chem.*, 2003, 68, 5534; H. J. Frohn and V. V. Bardin, *Z. Anorg. Allg. Chem.*, 2001, 627, 2499; S. Darses and J. P. Genet, *Eur. J. Org. Chem.*, 2003, 35, 4313.

(2) Synthesis of Cation

N-methylimidazole and ethyl chloride were allowed to react in an autoclave to synthesize 1-methyl-3-ethylimidazolium chloride (EMI$^+$Cl$^-$). Solvent and unreacted product were distilled off under reduced pressure to obtain a white solid, and the resulting white solid was purified by recrystallization using a mixture of solvents with different polarities in ethyl acetate.

(3) Synthesis of Ionic liquids

EMI-Cl and one of the potassium salts thus synthesized were mixed while stirring in anhydrous acetone for 12 hours. From each resulting mixture, a byproduct, KCl, was removed with a PTFE membrane filter, and then the acetone was removed under reduced pressure to obtain a desired ionic liquid. The resulting ionic liquid was further dissolved in dichloromethane, and a formed KCl solid precipitate was removed with a microfilter to increase the purity.

The physical properties of the resulting ionic liquids are as follows:

1-Ethyl-3-methylimidazolium methyltrifluoroborate (EMI [$CH_3BF_3$], 1):

Yield: 96%, slightly pale yellow liquid.

$^1$H NMR: δ=−0.44 (s, 3H), 1.54 (t, J=7.4 Hz, 3H), 4.04 (s, 3H), 4.39 (q, J=7.3 Hz, 2H), 7.75 (s, 1H), 7.83 (s, 1H), 9.48 ppm (s, 1H); $^{19}$F NMR: δ=132.4 ppm (q, $^1$J (B, F)=60.92 Hz); $^{11}$B NMR: δ=5.94 ppm (q, $^1$J (B, F)=61.59 Hz); FAB-MS, m/z (%): 111 (100) [EMI]$^+$, 83 (100) [$CH_3BF_3$]$^-$; elemental analysis calcd. for $C_7H_{14}BF_3N_2$(%): C, 43.34; H, 7.27; N, 14.44. found: C, 44.14; H, 7.07; N, 15.14.

1-Ethyl-3-methylimidazolium ethyltrifluoroborate (EMI [$C_2H_5BF_3$], 2):

Yield: 96%, slightly pale yellow liquid.

$^1$H NMR: δ=0.11 (s, 2H), 0.78 (t, J=6.8 Hz, 3H), 1.53 (t, J=7.4 Hz, 3H), 4.05 (s, 3H), 4.40 (q, J=7.3 Hz, 2H), 7.78 (s, 1H), 7.88 (s, 1H), 9.61 ppm (s, 1H); $^{19}$F NMR: δ=−139.8 ppm (q, $^1$J (B, F)=62.0 Hz); $^{11}$B NMR: δ=6.12 ppm (q, $^1$J (B, F)=63.8 Hz); FAB-MS, m/z (%): 111 (100) [EMI]$^+$, 97 (100) [$C_2H_5BF_3$]$^-$; elemental analysis calcd. for $C_8H_{16}BF_3N_2$(%): C, 46.19; H, 7.75; N, 13.47. found: C, 46.55; H, 7.60; N, 14.17.

1-Ethyl-3-methylimidazolium n-propyltrifluoroborate (EMI[n-$C_3H_7BF_3$], 3):

Yield: 97%, slightly pale yellow liquid.

$^1$H NMR: δ=0.15 (s, 2H), 0.86 (t, J=7.2 Hz, 3H), 1.29 (m, 2H), 1.54 (t, J=7.4 Hz, 3H), 4.03 (s, 3H), 4.38 (q, J=7.3 Hz, 2H), 7.72 (s, 1H), 7.80 (s, 1H), 9.30 ppm (s, 1H); $^{19}$F NMR: δ=−137.8 ppm (q, $^1$J (B, F)=58.91 Hz); $^{11}$B NMR: δ=6.12 ppm; (q, $^1$J (B, F)=62.57 Hz); FAB-MS, m/z (%): 111 (100) [EMI]$^+$, 111 (100) [n-$C_3H_7BF_3$]$^-$; elemental analysis calcd. for $C_9H_{18}BF_3N_2$(%): C, 48.68; H, 8.17; N, 12.62. found: C, 48.44; H, 8.06; N, 12.79.

1-Ethyl-3-methylimidazolium n-butyltrifluoroborate (EMI[n-$C_4H_9BF_3$], 4):

Yield: 97%, slightly pale yellow liquid.

$^1$H NMR: δ=0.15 (s, 2H), 0.83 (br s, 3H), 1.26 (m, 4H), 1.54 (t, J=7.4 Hz, 3H), 4.04 (s, 3H), 4.38 (q, J=7.3 Hz, 2H), 7.72 (s, 1H), 7.80 (s, 1H), 9.36 ppm (s, 1H); $^{19}$F NMR: δ=−137.8 ppm (q, $^1$J (B, F)=60.0 Hz); $^{11}$B NMR: δ=5.98 ppm (q, $^1$J (B, F)=63.5 Hz); FAB-MS, m/z (%): 111 (100) [EMI]$^+$, 125 (100) [n-$C_4H_9BF_3$]$^-$; elemental analysis calcd. for $C_{10}H_{22}BF_3N_2$(%): C, 50.87; H, 8.54; N, 11.87. found: C, 51.11; H, 8.58; N, 12.00.

1-Ethyl-3-methylimidazolium n-pentyltrifluoroborate (EMI[n-$C_5H_{11}BF_3$], 5):

Yield: 98%, slightly pale yellow liquid.

$^1$H NMR: δ=0.144 (s, 3H), 0.84 (t, J=7.4 Hz, 3H), 1.25 (br s, 3×2H), 1.54 (t, J=7.2 Hz, 3H), 4.03 (s, 3H), 4.38 (q, J=7.3 Hz, 2H), 7.72 (s, 1H), 7.79 (s, 1H), 9.23 ppm (s, 1H); $^{19}$F NMR: δ=−137.8 ppm (br s); $^{11}$B NMR: δ=5.99 ppm (q, $^1$J (B, F)=63.3 Hz); FAB-MS, m/z (%): 111 (100) [EMI]$^+$, 139

(100) [n-C$_5$H$_{11}$BF$_3$]$^-$; elemental analysis calcd. for C$_{11}$H$_{22}$BF$_3$N$_2$(%): C, 52.82; H, 8.87; N, 11.20. found: C, 52.53; H, 8.64; N, 11.16.

1-Ethyl-3-methylimidazolium vinyltrifluoroborate (EMI[CH$_2$=CHBF$_3$], 6):

Yield: 95%, slightly pale yellow liquid.

$^1$H NMR: δ=1.54 (t, J=7.4 Hz, 3H), 4.05 (s, 3H), 4.42 (q, J=7.3 Hz, 2H), 5.11 (br s, 1H), 5.25 (br s, 1H), 7.78 (s, 1H), 7.87 (s, 1H), 9.65 ppm (s, 1H); $^{19}$F NMR: δ=−140.2 ppm (q, $^1$J (B, F)=53.96 Hz, 3F; BF$_3$); $^{11}$B NMR: δ=3.22 ppm (q, $^1$J (B, F)=54.42 Hz, BF$_3$); FAB-MS, m/z (%): 111 (100) [EMI]$^+$, 95 (100) [CH$_2$=CHBF$_3$]$^-$; elemental analysis calcd. for C$_8$H$_{14}$BF$_3$N$_2$(%): C, 46.64; H, 6.85; N, 13.60. found: C, 47.14; H, 6.84; N, 13.70.

1-Ethyl-3-methylimidazolium trifluorovinyltrifluoroborate (EMI[CF$_2$=CFBF$_3$], 7):

Yield: 96%, slightly pale yellow liquid.

$^1$H NMR: δ=1.57 (t, J=7.4 Hz, 3H), 4.04 (s, 3H), 4.38 (q, J=7.2 Hz, 2H), 7.68 (s, 1H), 7.76 (s, 1H), 8.97 ppm (s, 1H); $^{19}$F NMR: δ=−103.2 ppm (br s, 1F), 125.3 (m, 1F), 143.0 (q, $^1$J (B, F)=39 Hz, 3F), 194.2 ppm (br s, 1F); $^{11}$B NMR: δ=1.31 ppm (qdd, $^1$J (B, F)=40 Hz, $^2$J (B,F-1)=24 Hz, $^3$J (B, trans-F-2)=7 Hz); FAB-MS, m/z (%): 111 (100) [EMI]$^+$, 149 (100) [CF$_2$=CFBF$_3$]$^-$; elemental analysis calcd. for C$_8$H$_{11}$BF$_6$N$_2$ (%): C, 36.96; H, 4.26; N, 10.77. found: C, 36.81; H, 4.08; N, 10.84.

Table 1 below shows additional physical properties for the compounds listed above:

TABLE 1

| Salts | T$_g$/ °C. | T$_c$/ °C. | T$_m$/ °C. | T$_d$/ °C. | d/ g mL$^{-1}$ | η/ cP | κ/ mScm$^{-1}$ |
|---|---|---|---|---|---|---|---|
| 1 | −93 | | | 272 | 1.15 | 47 | 9.0 |
| 2 | −89 | | | 258 | 1.13 | 72 | 6.3 |
| 3 | −87 | −49 | −14 | 281 | 1.11 | 52 | 5.7 |
| 4 | −85 | −29 | −9 | 249 | 1.082 | 83 | 3.2 |
| 5 | | | 16 | 292 | 1.065 | 88 | 2.7 |
| 6 | −106 | | | 227 | 1.16 | 41 | 10.5 |
| 7 | −111 | | | 242 | 1.35 | 16 | 17.7 |
| EMI[BF$_4$]$^b$ | −93 | −60 | 15 | 420 | 1.28 | 42 | 13.6 |

In Table 1, d denotes density at 25° C.; Tg, glass transition temperature; Tc, crystallization temperature; Tm, melting point; η, viscosity at 25° C.; and κ, electrical conductivity at 25° C.

The results presented above establish that the ionic liquids according to the invention have low melting points, high conductivities and low viscosities, and hence exhibit excellent properties for use in electrochemical devices and as solvents for organic reactions.

INDUSTRIAL APPLICABILITY

The ionic liquids according to the invention are capable of easily dissolving electrolytes such as lithium salts, and are also nonflammable and have low viscosities; therefore, the ionic liquids are suitable for use as electrolyte solvents for lithium batteries such as lithium secondary batteries, electric double-layer capacitors, and the like.

The ionic liquids according to the invention are suitable for use in electrochemical devices such as lithium secondary batteries, fuel cells, solar batteries, electrical double-layer capacitors and the like; as solvents for chemical reactions; and as lubricants.

The invention claimed is:

1. An ionic liquid comprising an imidazolium ion represented by the formula:

wherein each of Y$^1$ and Y$^2$, which may be the same or different, is methyl, ethyl, n-propyl, isopropyl, n-butyl, isobutyl, sec-butyl, or tert-butyl; and an anion represented by [CF$_2$=CFBF$_3$]$^-$.

2. An ionic liquid according to claim 1, wherein the cation is a 1-methyl-3-ethylimidazolium cation.

3. A lithium battery comprising an ionic liquid according to claim 1.

4. A process for preparing an ionic liquid, comprising mixing a compound including an imidazolium compound represented by the formula:

wherein each of Y$^1$ and Y$^2$, which may be the same or different, is methyl, ethyl, n-propyl, isopropyl, n-butyl, isobutyl, sec-butyl, or tert-butyl,
with a compound including, as an anionic component, an anion represented by [Z—BF$_3$]—, wherein Z is a perfluorovinyl group (CF$_2$=CF).

5. A lithium battery comprising an ionic liquid according to claim 2.

* * * * *